United States Patent [19]
Dhein et al.

[11] Patent Number: 5,190,932
[45] Date of Patent: Mar. 2, 1993

[54] MICROBICIDAL FORMULATIONS COMPRISING WATER DISPERSIBLE POLYMERS WITH CHEMICALLY BONDED AMMONIUM GROUPS AND FATTY ACID RADICALS

[75] Inventors: Rolf Dhein, Krefeld; Lothar Bäcker, Dormagen; Otto Exner, Monheim; Walter Radt, Krefeld; Ingrid Radt, Krefeld; Christian Radt, Krefeld; Hans G. Schmitt, Krefeld, all of Fed. Rep. of Germany

[73] Assignee: Bayer Aktiengesellschaft, Leverkusen, Fed. Rep. of Germany

[21] Appl. No.: 551,591

[22] Filed: Jul. 11, 1990

[30] Foreign Application Priority Data

Jul. 25, 1989 [DE] Fed. Rep. of Germany ....... 3924527

[51] Int. Cl.$^5$ ..................... A01N 31/08; A01N 43/52; A01N 55/04; A01N 57/14
[52] U.S. Cl. .................................. 514/112; 514/367; 514/372; 514/383; 514/388; 514/478; 514/493; 514/516; 514/736; 514/737
[58] Field of Search ............... 514/736, 112, 367, 372, 514/383, 478, 493, 516, 388, 737

[56] References Cited

U.S. PATENT DOCUMENTS

| | | | |
|---|---|---|---|
| 3,932,684 | 1/1976 | Lauermann et al. | 424/346 |
| 4,900,721 | 2/1990 | Bansemir et al. | 514/25 |
| 4,909,915 | 3/1990 | Bederke et al. | 204/181.4 |

FOREIGN PATENT DOCUMENTS

| | | |
|---|---|---|
| 0286009 | 10/1988 | European Pat. Off. |
| 0331528 | 9/1989 | European Pat. Off. |
| 1556365 | 11/1979 | United Kingdom |
| 2203340 | 10/1988 | United Kingdom |

*Primary Examiner*—Richard L. Raymond
*Assistant Examiner*—S. Mark Clardy
*Attorney, Agent, or Firm*—Sprung, Horn, Kramer & Woods

[57] ABSTRACT

The invention relates to the use of water-soluble polymers containing chemically bonded tertiary and/or quaternary ammonium groups as auxiliaries for formulating microbicides, the microbicide formulations prepared using these water-soluble polymers and the use of these formulations for preserving industrial materials.

8 Claims, No Drawings

MICROBICIDAL FORMULATIONS COMPRISING WATER DISPERSIBLE POLYMERS WITH CHEMICALLY BONDED AMMONIUM GROUPS AND FATTY ACID RADICALS

The invention relates to the use of special polymers, namely water-dispersible polymers, having a specific content of chemically bonded tertiary and/or quaternary ammonium groups, as auxiliaries for the formulation of microbicides, the microbicidal formulations prepared using these polymers and the use of these formulations for preserving industrial materials.

Although the active compounds which are often employed today for the microbicidal treatment of industrial materials, for example wood, textiles, leather and paper, have very good microbicidal activity, they can only be converted into the aqueous formulations required in practice with great difficulty owing to their insolubility or poor solubility in water, and in addition they do not adhere adequately to the materials to be preserved. Such active compounds which are difficult to convert into aqueous formulations are, above all, phenolic microbicides such as o-phenylphenol, p-chloro-m-cresol and 5,5'-dichloro-2,2'-dihydroxydiphenylmethane, as well as 2-thiocyanatomethyl-thiobenzothiazole, benzimidazolylmethyl carbamate (BCM), methylene bisthiocyanate, tributyl-tin salts, 3-iodo-2-propinyl-butyl carbamate, 2-N-octyl-4-isothiazolin-3-one, α-(diethoxy-thiophosphoryloximino)-phenylacetonitrile, α-[2-(4-chlorophenyl)-ethyl]-α-(1,1-dimethylethyl)-1H-1,2,4-triazol-1-ethanol (tebuconazol) and the mixtures of these active compounds.

To overcome the difficulties in the preparation of aqueous formulations the phenolic active compounds have hitherto been used in the form of aqueous solutions of their alkali metal salts. However, these strongly alkaline formulations—a 1% strength aqueous solution of the sodium salt of o-phenylphenol has a pH value of 11.3—have the disadvantage that they are highly caustic and their use therefore requires considerable safety measures for reasons of work safety and hygiene. The fixation of the alkali metal salts of the phenolic active compounds onto the materials to be preserved is also inadequate.

The alkaline formulations also have the disadvantage that they are incompatible with the acid-reacting water-repellents simultaneously used for the rotproofing of textile materials. A complicated two-bath process is therefore necessary for the application of the microbicide and the water-repellent. In the first bath the textile material is treated with the alkaline active compound formulation. After the textile materials have been dried and neutralised with acetic acid they are treated in a second bath with the acid water-repellent. To avoid this complicated two-bath process attempts have therefore been made to render the phenolic active compounds compatible with the acid water-repellents by means of esterification (see German Offenlegungsschrift No. 30 31 933). In addition, the alkaline formulations have the disadvantage that they do not allow the phenolic active compounds to be applied together with other non-phenolic microbicides, since the non-phenolic active compounds are in most cases not alkali-resistant.

According to European Application No. 286 009 another possibility of converting poorly soluble phenolic microbicides into a usable form consists in employing solutions of these microbicides in organic solvents in combination with aqueous solutions or mixtures of polymeric binders. However, for safety-related, ecological and practical reasons (the microbicides, despite their poor solubility, are washed out of the treated materials too rapidly on exposure to weathering), these formulations do not satisfy the demands placed on them in practice. The same applies to the microbicidal formulations described in German Patent Specification No. 30 04 248, which also contain emulsifiers in addition to the organic solvents.

Although organic solvents for the microbicides are dispensed with in the microbicidal formulations described in German Offenlegungsschrifts Nos. 30 04 319 and 30 04 249 and non-ionic emulsifiers and cationic low molecular weight wetting agents are used instead, these formulations have the disadvantage that the emulsions produced by dilution with water are only stable under limited conditions and, above all, the active compounds applied to the materials to be preserved are washed out too rapidly.

It is also known that both low molecular weight quaternary ammonium compounds (see British Application No. 20 10 851) and high molecular weight (polymeric) quaternary ammonium compounds (see European Applications Nos. 286 009, 331 528 and 355 316, as well as Vysokomol. Soedin. 20 (1978), Ser. B., No. 1, pages 45–48) have microbicidal action. However, compared with the microbicidal action of phenolic microbicides, that of the aforementioned monomolecular and polymeric ammonium compounds is only minimal and completely inadequate for the effective preservation of materials. In addition, owing to their high substantivity on the materials to be preserved, in particular wood and other cellulose materials, these quaternary ammonium compounds do not penetrate as deeply as required and become only unevenly spread over the surfaces. This so-called "spotting effect" means that the materials treated with the ammonium compounds are partially susceptible towards microbes.

The object was therefore to find auxiliaries for the preparation of aqueous formulations of microbicides which are insoluble or only poorly soluble in water, in particular phenolic active compounds, with the aid of which it is possible to prepare stable, aqueous, non-caustic microbicidal formulations which have a high penetrating power on the materials to be treated and which spread uniformly over the surfaces of the materials to be treated and with the aid of which it is possible to fix the active compounds onto the materials to be preserved as completely and permanently as possible.

It has surprisingly been found that, with the aid of water-dispersible polymers which have a specific content of chemically bonded tertiary and/or quaternary ammonium groups, stable, aqueous, neutral to weakly acidic, easy-to-handle microbicidal formulations are obtained which have the desired penetrating and spreading capacity and with the aid of which the desired complete and permanent fixing of the formulated active compounds on the materials to be preserved is achieved.

The formulations obtained with the aid of these special polymers surprisingly display considerably improved microbicidal action with respect to longterm effects and temperature resistance compared with the microbicidal action of the active compounds to be formulated and the microbicidal action of the known polymers containing quaternary ammonium groups. In addition, the formulations are distinguished by very high compatibility with the acid-reacting water-repellents usually employed for the rotproofing of textile materials, so that these formulations can be applied directly, together with said repellents, as well as with all the other additives and auxiliaries in a one-bath process.

The invention therefore relates to the use of water-dispersible polymers which have a content of 70 to 500 milliequivalents (meqs) of chemically bonded tertiary and/or quaternary ammonium groups per 100 g of polymer, as auxiliaries for the preparation of water-containing and water-dilutable formulations of microbicidal active compounds, in particular active compounds which are insoluble or only poorly soluble in water.

Poly(meth)acrylates and polyurethanes have proved to be particularly suitable water-dispersible polymers having a content of 70 to 500 meqs of chemically bonded tertiary and/or quaternary ammonium groups per 100 g of polymer.

In addition to their good emulsifying and stabilising action and their advantageous property of substantially improving the depth of penetration, the spreading capacity and the adhesion of the microbicidal active compounds into, over and to the treated industrial materials, and thus of effectively increasing the uniformity and stability of the microbicidal finish, the polymers to be used as formulation auxiliaries according to the invention have the additional advantageous property that the microbicidal formulations prepared therewith only insignificantly change the appearance of the surfaces of the treated industrial materials, for example wood.

The content of chemically bonded tertiary and/or quaternary ammonium groups in the polymers to be used according to the invention has a crucial influence on the emulsifying effect of the polymers and the properties of the formulations prepared therewith. The polymers to be used according to the invention preferably have a content of 100 to 400 meqs of chemically bonded tertiary and/or quaternary ammonium groups per 100 g of polymer.

In addition to the 70 to 500 meqs of chemically bonded tertiary and/or quaternary ammonium groups per 100 g of polymer, the polymers to be used according to the invention can also contain chemically bonded radicals of mono- or polyunsaturated fatty acids. The quantity of chemically bonded mono-or polyunsaturated fatty acid radicals can be 5 to 40% by weight, based on the total weight of the polymer.

Polymers containing fatty acid radicals have proven to be particularly suitable for the formulations of phenolic active compounds for the microbicidal treatment of wood. A particularly good penetrating capacity and thus an effective fixation of the active compounds onto and in the wood is achieved with these polymers.

Poly(meth)acrylates which are obtained by reacting copolymers of styrene, methyl methacrylate, glycidyl methacrylate and, if appropriate, n-butyl acrylate with 5–40% by weight of unsaturated fatty acids and 5–25% by weight of diethylamine or dimethyl-(1-hydroxyethyl)-ammonium acetate, all the % by weight being based on the total weight of the polymer, are suitable as the water-dispersible polymers with the stated content of chemically bonded tertiary and/or quaternary ammonium groups to be used according to the invention.

Of these poly(meth)acrylates the reaction products of those copolymers in which the proportion of the individual monomers is as follows:

| | |
|---|---|
| styrene: | 10–40% by weight |
| methyl methacrylate: | 5–20% by weight |
| glycidyl methacrylate: | 20–50% by weight |
| n-butyl acrylate: | 0–10% by weight. | all the % by weight being based on the total weight of the copolymer, are particularly preferred.

Poly(meth)acrylates which are furthermore preferably used are those polymers with the stated content of chemically bonded tertiary and/or quaternary ammonium groups which have been obtained by the copolymerisation of styrene, methyl methacrylate, N,N-dimethylaminoethyl methacrylate and, if appropriate, n-butyl acrylate; those copolymers are particularly preferred in which the proportions of the individual monomers are as follows:

| | |
|---|---|
| styrene: | 10–50% by weight |
| methyl methacrylate: | 5–30% by weight |
| N,N-dimethylaminoethyl methacrylate: | 20–60% by weight |
| n-butyl acrylate: | 0–10% by weight. |

These water-dispersible polymers usable according to the invention which are based on (meth)acrylates and have the stated content of chemically bonded tertiary and/or quaternary ammonium groups and, if appropriate, chemically bonded radicals of unsaturated fatty acids, can be obtained by various methods. They can be prepared, for example, by reacting poly(meth)acrylates containing epoxide groups with secondary amines and/or tertiary amine salts or by the direct copolymerisation of (meth)acrylic acid esters with (meth)acrylic acid derivatives (esters, amides) containing tertiary amino groups and/or quaternary ammonium groups and—if secondary amines or (meth)acrylic acid derivatives containing tertiary amino groups are used—subsequent salt formation by the addition of acids. The preparation of the water-dispersible poly(meth)acrylates containing chemically bonded tertiary ammonium groups and chemically bonded radicals of unsaturated fatty acids is described in German Offenlegungsschrift No. 3 738 932.

The poly(meth)acrylates containing epoxide groups which are required as starting compounds are known and/or are obtainable by known processes (see Houben-Weyl, 4th edition, Volume 14/1, page 24 et seq.) by free radical copolymerisation of (meth)acrylic acid derivatives, such as glycidyl (meth)acrylates and (meth)acrylic acid esters, such as methyl methacrylate, methyl acrylate and n- and i-butyl, n-hexyl, cyclohexyl, 2-ethylhexyl, 2-hydroxyethyl, hydroxypropyl, 2-ethoxyethyl and 2-butoxyethyl methacrylate. Other monomers, such as vinylically unsaturated hydrocarbons, such as styrene and vinyltoluene, can also additionally be used in the copolymerisation. The proportion of these other monomers in the polymers containing epoxide groups should not exceed 70 mol % and is preferably 5–60 mol % (mol % based on the total number of moles of the monomers in the polymer). The molecular weight of the polymers is higher than 700, preferably 1,000 to 20,000. The poly(meth)acrylates containing epoxide groups should have epoxide equivalent weights of 150 to 1,300, preferably 150 to 700.

To prepare the polymers containing chemically bonded radicals of unsaturated fatty acids these poly(meth)acrylates containing epoxide groups are, for example, first reacted in an inert gas atmosphere at 80° to 120° C. with a quantity of unsaturated fatty acids corresponding to the desired content of unsaturated fatty acid radicals and then with a quantity of secondary amines and/or salts of tertiary amines corresponding to the desired content of tertiary and/or quaternary ammonium groups.

The fatty acids react with the epoxide groups to form ester groups. The epoxide groups still remaining after the reaction are then converted into the tertiary and/or quaternary ammonium groups by reaction with the secondary amines and/or salts of tertiary amines.

The unsaturated fatty acids used are the known naturally occurring or synthetic, drying fatty acids containing two or more double bonds and up to 22, preferably 14 to 18, C atoms. Examples of such fatty acids are linoleic acid, linolenic acid, eleostearic acid, parinaric acid, arachidonic acid, clupanodonic acid, misic acid, ricinenic fatty acid and mixture of conjugated polyunsaturated fatty acids of the kind available, for example, under the tradenames ®Prifac 7967, ®Prifac 7968 and ®Prifac 7969. The last three acid mixtures mentioned are mixtures of synthetic, conjugated, unsaturated $C_{18}$ fatty acids.

To prepare polymers which contain only chemically bonded tertiary and/or quaternary ammonium groups the poly(meth)acrylates containing epoxide groups are reacted directly with the quantities of secondary amines and/or salts of tertiary corresponding to the desired content of chemically bonded tertiary and/or quaternary ammonium groups.

To prepare the water-dispersible poly(meth)acrylates with the stated content of chemically bonded tertiary and/or quaternary ammonium groups which are to be used according to the invention, secondary amines, such as dimethylamine, diethylamine, dipropylamine, di-n-butylamine, diethanolamine and diisopropanolamine, and, as the salts of tertiary amines, particularly the salts, for example acetates, of trimethylamine, triethylamine, N,N-dimethyl-ethanolamine, N,N-diethylethanolamine, N-methyl-diethanolamine, N-butyl-diethanolamine, 3-diethylamino-1-propanol, 1-dimethylamino-2-propanol and triethanolamine have proven to be particularly suitable. The use of the salts of N,N-dimethylethanolamine is particularly advantageous, because the poly(meth)acrylates containing quaternary ammonium groups prepared therefrom have particularly good solubility in water.

The reaction of the poly(meth)acrylates containing epoxide groups with the secondary amines and/or salts of tertiary amines is preferably carried out at temperatures of 60° to 100° C. Mixtures of secondary amines and salts of tertiary amines are used for the preparation of poly(meth)acrylates containing tertiary and quaternary ammonium groups. Whilst the polymers containing quaternary ammonium groups which are obtainable by reaction with the salts of tertiary amines are directly soluble in water, the polymers containing tertiary amino groups which are obtainable by reaction with the secondary amines must be rendered water-soluble by neutralisation with acids. Organic carboxylic acids having 1 to 5 C atoms, such as formic acid, acetic acid, propionic acid, malic acid or dimethylolpropionic acid, are particularly suitable for the neutralisation.

The preparation of the water-dispersible polymers with the stated content of chemically bonded tertiary and/or quaternary ammonium groups which are to be used according to the invention by copolymerisation of (meth)acrylate acid derivatives and (meth)acrylic acid esters containing tertiary amino groups and/or quaternary ammonium groups is known (see Houben-Weyl, 4th edition, Vol. 14/1, page 24 et seq.) Examples which may be mentioned of representatives of (meth)acrylic acid derivatives containing tertiary amino groups or quaternary ammonium groups are: N,N-dimethylaminoethyl methacrylate, N,N-dimethylaminopropyl-methacrylamide, 2-trimethylammoniumethyl methacrylate chloride, N-trimethylammonium propylmethacrylamide chloride, N,N-dimethylaminoethyl acrylate and 2-trimethylammoniumethyl acrylate chloride. If the monomers already present in the form of a salt are used, subsequent neutralisation of the polymer obtained is not necessary. The polymer salts obtained by copolymerisation can be directly diluted with water. In contrast, the polymers containing tertiary amino groups must be neutralised with acids, preferably organic acids, such as the abovementioned $C_1$–$C_5$ carboxylic acids, before dilution with water.

Polycondensates of the polyurethane type are additionally suitable as water-dispersible polymers having the stated content of chemically bonded tertiary and/or quaternary ammonium groups to be used according to the invention.

The polyurethanes containing chemically bonded tertiary and/or quaternary ammonium groups are prepared by known processes [see Houben-Weyl, 4th edition, "Makromolekulare Stoffe" (Macromolecular Materials), Part 2, page 1561 et seq.] by the polyaddition of components containing isocyanate-reactive hydrogen atoms, such as polyalcohols, and polyesters and polyethers containing terminal OH groups, in the presence of tertiary amines containing one or more hydroxyl groups, with the proviso that the contents of chemically bonded tertiary and/or quaternary ammonium groups required according to the invention are 70 to 500, preferably 100 to 400 meqs per 100 g of polyurethane.

Both single-stage and multi-stage processes are suitable for the preparation of the polyurethanes to be used according to the invention. Thus polyesters or polyethers containing terminal hydroxyl groups can, for example, be prepared in the first stage by polycondensation of polyols and polycarboxylic acids or by polymerisation of epoxides such as ethylene oxide, propylene oxide, butylene oxide and tetrahydrofuran, and can then be reacted, in combination with hydroxyfunctional tertiary amines, with polyisocyanates to form the polyurethane.

Suitable tertiary amines containing hydroxyl groups are, for example, N-methyldiethanolamine, N-butyldiethanolamine, bis-(2-hydroxypropyl)-methylamine, 2,2'-(9-octadecenylimino)-bisethanol, trithanolamine, tris-[2-(2-hydroxyethoxy)-ethyl]-amine, triisopropanolamine, 2-(hydroxyethyl)-bis-(2-hydroxypropyl)-amine and 2,2-bis(hydroxymethyl)-N,N-dimethyl-1-butanamine.

In addition to these amines with more than one hydroxyl group portions of acyclic tertiary monoamines with one hydroxyl group, such as, for example, N,N-dimethylethanolamine, 2-[(2-dimethylamino)ethoxy]-ethanol, 2-(diethylamino)-ethanol, 2-[(2-diethylamino)-ethoxy]-ethanol and 2-(dibutylamino)-ethanol can be used. This list of the suitable tertiary amines containing hydroxyl groups makes no claim to completeness, but only mentions examples of possible representatives from this class of compounds.

Owing to the lack of reactive hydrogen atoms on the nitrogen atom these amines react with their hydroxyl groups to form urethanes in the reaction with polyisocyanates. In the case of polyhydroxy-functional amines the tertiary amino group becomes part of the polymer chain and, in the case of monohydroxy-functional amines, becomes terminally bonded to the polymer chain.

Epoxide resins based on aliphatic polyols, such as, for example, ®Epikote 160, ®Epikote 162, ®Epikote 812 (commercial product of the German Shell company) or aromatic diglycidyl ethers based on 2,2-bis(4-hydroxyphenyl)-propane, such as, for example, ®Lekutherm X 18, ®Lekutherm X 20, ®Lekutherm X 23, ®Lekutherm X 24 (commercial products of Bayer AG) are also suitable for the preparation of the polyurethanes to be used according to the invention. By opening the epoxide ring with secondary amines and/or salts of tertiary amines, diols containing tertiary amino groups and/or quaternary ammonium groups are obtained, which are then reacted to form a polyurethane in a second reaction step by reaction with diisocyanates.

Prior to the reaction with secondary amines and/or salts of tertiary amines, mono- or polyunsaturated fatty acids can also be added to some of the existing epoxide groups. The fatty acids react with the epoxide groups to form ester groups. The epoxide groups still remaining after the reaction are then opened by reaction with secondary amines and/or salts of tertiary amines, whereupon diols containing tertiary amino groups and/or quaternary ammonium groups are obtained.

The polyurethanes to be used according to the invention preferably consist to an extent of up to 70% by weight of low molecular weight epoxides or epoxide resins with molecular weights of 200–2000 g/mole. The low viscosity epoxides are preferably diglycidyl ethers of aliphatic and/or aromatic diols.

Those unsaturated fatty acids which have already been mentioned above for the preparation of the poly(meth)acrylates containing unsaturated fatty acid radicals are used as the unsaturated fatty acids.

Suitable secondary amines for opening the epoxide ring of epoxide resins are, for example, dimethylamin, diethylamin, dipropylamine, di-n-butylamine, diisopropylamine and diisobutylamine and the salts, for example, acetates of trimethylamine, triethylamine, N,N-dimethyl-ethanolamine, N,N-diethyl-ethanolamine, N-methyl-diethanolamine, N-butyldiethanolamine, 3-diethylamino-1-propanol, 1-dimethylamino-2-propanol and triethanolamine, have proven to be particularly suitable as the salts of tertiary amines.

A further suitable process for the preparation of the polyurethanes containing quaternary ammonium groups to be used according to the invention is the reaction, proceeding in accordance with urethane formation, of a diisocyanate with an acyclic tertiary monoamine having one hydroxyl group. The reaction is carried out in such a manner that both isocyanate groups of the diisocyanate are reacted with the monoamine. The resulting intermediate product containing urethane groups has terminal tertiary amino groups. By adding an acid the amino groups are protonated and converted into tertiary ammonium groups. The H atom located on the ammonium nitrogen atom can then be used for the reaction with epoxide resins. In this reaction the epoxide ring is opened with the formation of quaternary ammonium groups and water-dilutable polyurethanes are formed.

Suitable epoxide resins in the context of this reaction are, for example, ®Epikote 160, ®Epikote 162, ®Epikote 812 or aromatic diglycidyl ethers based on 2,2-bis-(4-hydroxyphenyl)-propane, such as, for example, ®Lekutherm X 12, ®Lekutherm X 20, ®Lekutherm X 23 and ®Lekutherm X 24.

Tertiary amines with one hydroxyl group which are suitable for the preliminary reaction of the diisocyanate with the amine are, for example, N,N-dimethyle-thanolamine and 2-[(2-dimethylamino)-ethoxy]-ethanol.

Isocyanates suitable for the preparation of the polyurethanes to be used according to the invention which can be prepared by the abovementioned processes are aliphatic, cycloaliphatic, araliphatic, aromatic and heterocyclic polyisocyanates of the kind described, for example by W. Siefken in Justus Liebig's "Annalen der Chemie", 562, pages 75 to 136.

Examples of such polyisocyanates which can also be used as mixtures are: 1,6-hexamethylene diisocyanate, cyclohexane-1,3- and -1,4-diisocyanate or mixtures of these isomers, 5-isocyanato-3-(isocyanato-methyl)-1,1,3-trimethylcyclohexane, bis-[4-isocyanato-cyclohexyl]-methane, 1,3-bis-[isocyanato-methyl]-benzene, 1,4-bis-]2-isocyanato-ethyl]-cyclohexane, 1,3-bis-[isocyanato-methyl]-cyclohexane, 1,3- and 1,4-phenylenediisocyanate, 2,4- and 2,6-toluylenediisocyanate and mixtures of these isomers, bis-[2-isocyanato-phenyl]-methane, (2-isocyanato-phenyl)-(4-isocyanato-phenyl)-methane, bis-[4-isocyanato-phenyl]-methane, 1,5-bis-[isocyanato]-naphthalene and 4,4'-bis-[isocyanato]-3,3'-dimethyl-biphenyl.

Polyisocyanates with more than two isocyanate groups can also be used. However, the above-mentioned diisocyanates are preferably used and 5-isocyanato-3-(isocyanato-methyl)-1,1,3-trimethylcyclohexane is particularly preferably used.

Before being diluted with water the polyurethanes containing tertiary amino groups must first be neutralised with acids, preferably with the $C_1$–$C_5$ carboxylic acids mentioned for the poly(meth)acrylates.

Following the preparation of the water-dispersible polymers with the stated content of chemically bonded tertiary and/or quaternary ammonium groups to be used according to the invention, the polymers can be converted into 10 to 50% strength by weight aqueous polymer concentrates by the addition of water and these aqueous polymer concentrates can be used for the formulation of the microbicides which are insoluble or only poorly soluble in water. It is, however, also possible to mix the polymers directly with the microbicide and to dilute this mixture with water to the desired concentration. The formulations according to the invention can be prepared, for example, by a procedure in which the microbicides present in liquid or liquefied form (for example in molten form or dissolved in a small quantity of organic solvents) are added slowly, with stirring, to a prescribed quantity of the aqueous polymer concentrate. In this manner aqueous microbicidal formulations having active compound contents of up to 45% by weight can be prepared; formulations having active compound contents of 20 to 40% by weight and polymer contents of 10 to 30% by weight (all the % by weight being based on the weight of the finished formulation) have proven suitable for use in practice; the water content of these formulations can be between 15 and 65% by weight and their content of organic solvents can be between 5 and 15% by weight (all the % by weight being based on the weight of the finished formulations).

For the stability of the microbicidal formulations prepared according to the invention and the permanent fixing of the microbicides onto the materials to be preserved, it has proven appopriate to match the quantities in the formulations of polymers and microbicides to be used according to the invention in such a manner that 0.5–7.0 moles of active compound are present per equivalent of ammonium groups in the polymer. This ratio of ammonium groups to active compound is generally obtained if the ratio by weight of polymer to microbicide in the microbicidal formulations is 1:0.1 to 2.

The aqueous polymer concentrates to be used as formulation auxiliaries according to the invention are suitable for the preparation of stable formulations of microbicides which are insoluble or only poorly soluble in water, such as thiocyanomethylthiobenzothiazole, benzimidazolylmethyl carbamate, methylenebisthiocyanate, tebuconazol, tributyl-tin salts and above all phenolic microbicides, such as o-phenylphenol, p-chloro-m-cresol and 2,2'-dihydroxy-5,5'-dichlorodiphenylmethane.

In addition to the water-dispersible polymers having the stated content of chemically bonded tertiary and/or quaternary ammonium groups, microbicides and water, the formulations according to the invention can also contain organic solvents and/or auxiliaries and additives known from coating technology, such as pigments, fillers, flow control auxiliaries and drying agents. It should, however, be emphasised that it is one of the advantages of the formulations according to the invention that their content of organic solvents is very low, and in general can be less than 10% by weight, based on the weight of the finished formulation. Suitable organic solvents are, for example, butyl glycol, methoxypropanol, ethylene glycol monoethyl ether, butoxypropanol or mixtures of such solvents. The auxiliaries and additives can either originate from the starting materials for the preparation of the formulations according to the invention or can be added separately to the finished formulations.

The invention also relates to the water-containing and water-dilutable microbicidal formulations obtainable according to the invention. These formulations are characterised by the fact that they contain water-dispersible polymers having a content of 70 to 500 meqs of the chemically bonded tertiary and/or quaternary ammonium groups, preferably poly(meth)acrylates or polyurethanes, microbicides, water, organic solvents and, if appropriate, auxiliaries and additives known from coating technology.

The microbicidal formulations according to the invention are generally suitable for the microbicidal treatment of industrial materials. Examples which may be mentioned of such industrial materials are: adhesives, sizes, paper, card, textiles, leather, wood, paints and plastic articles, cooling lubricants and other materials which may be attacked or decomposed by microorganisms. Components of production plants, for example cooling water circulations, the functioning of which may be impaired by the multiplication of microorganisms, may also be mentioned as industrial materials to be preserved. The microbicidal formulations according to the invention are particularly preferably suitable for the microbicidal treatment of wood, textiles, leather and paper.

The invention therefore also relates to the use of the microbicidal formulations according to the invention, if appropriate in dilute form, for the microbicidal treatment of industrial materials, in particular for the treatment of wood, textiles, leather and paper.

Examples which may be mentioned of microorganisms which can cause degradation or a change in the industrial materials are bacteria, fungi, yeasts, algae and slime organisms. The active compounds according to the invention preferentially act against fungi, in particular moulds, fungi which permanently discolour wood and wood-destroying fungi, and against slime organisms and algae.

Microorganisms of the following genera may be mentioned as examples:

Alternaria, such as *Alternaria tenuis,*
Aspergillus, such as *Aspergillus niger,*
Chaetomium, such as *Chaetomium globosum,*
Coniophora, such as *Coniophora puteana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,* and
Staphylococcus, such as *Staphylococcus aureus.*

The parts mentioned in the following examples are parts by weight, unless stated otherwise.

EXAMPLE 1

810 parts of o-phenylphenol are added slowly at room temperature, with vigorous stirring, to 3,100 parts of an aqueous polymer solution of the following composition:

| | |
|---|---|
| 31.6% | by weight of a water-soluble copolymer containing 211.2 meqs of a polymer containing chemically bonded tertiary ammonium groups per 100 g of polymer |
| 9.7% | by weight of methoxypropanol |
| 4.0% | by weight of acetic acid |
| 54.7% | by weight of distilled water |
| 100% | by weight. |

A stable emulsion of the following composition is obtained:

| | |
|---|---|
| 26.4% | by weight of a water-soluble copolymer containing 211.1 meqs of chemically bonded tertiary amino groups per 100 g of polymer |
| 8.1% | by weight of methoxypropanol |
| 3.3% | by weight of acetic acid |
| 41.5% | by weight of distilled water |
| 20.7% | by weight of o-phenylphenol |
| 100% | by weight. | pH value of the emulsion: 4.85; viscosity: 121 mPas.

The ratio of equivalents of ammonium groups to moles of microbicide is 1:2.18.

The emulsion can be diluted without difficulty with water to active compound concentrations of 1 to 5% by weight.

The aqueous polymer solution used had been obtained as follows:

a) A mixture of 738.7 parts of styrene, 330 parts of methyl methacrylate, 35 parts of n-butyl acrylate, 931 parts of glycidyl methacrylate, 45.7 parts of azo-bis-isobutyronitrile and 19.9 parts of dodecanethiol was added dropwise with stirring at 110° C. in the course of 2.5 hours to 899.8 parts of methoxypropanol. After post-reacting the mixture for 8 hours at 110° C. the polymerization was complete (determined by heating a sample to 120° C. for one hour and weighing out the non-volatile constituents).

The solids contents of the reaction product was 70.3% by weight; the flow viscosity (according to DIN 53 211) of the polymerisation product diluted with methoxypropanol to form a 40% strength solution was: 87 seconds.

b) 2,774.1 parts of the 70.3% strength by weight polymer solution described under a) were reacted under nitrogen for 4 hours at 120° C. with 282.1 parts of a mixture of unsaturated $C_{18}$ carboxylic acids (Prifac 7968) (acid number of the reaction product: ~0.1).

The flow viscosity of the copolymer solution diluted with methoxypropanol to form a 40% strength by weight solution was: 52 seconds. Solids content of the reaction mixture: 72.6% by weight.

c) 2,000 parts of the copolymer solution described under b) were added with stirring, in the course of 30 minutes, to 265 parts of diethylamine which had been heated to 50° C., during which the temperature rose to 100° C.

The reaction mixture is stirred for a further 3.5 hours at 100° to 110° C., and then 24.1 parts of diethylamine and 18.9 parts of methoxypropanol are distilled off under reduced pressure.

The copolymer obtained had a content of tertiary amino groups of 211.2 meqs per 100 g of polymer. The solids content of the reaction product was 76.6% by weight. The flow viscosity of the reaction mixture diluted with methoxypropanol to 40% by weight was: 79 seconds. By adding glacial acetic acid the amino groups were converted into ammonium groups and the reaction product was diluted to a solids content of 31.6% by weight by adding water in portions. A clear solution of the following composition was obtained:

| | |
|---|---|
| 31.6% | by weight of a water-soluble copolymer containing tertiary ammonium groups |
| 9.7% | by weight of methoxypropanol |
| 4.0% | by weight of acetic acid |
| 54.7% | by weight of distilled water |
| 100% | by weight |

The pH value of the solution was: 5.42
Viscosity: 1.170 mPas

EXAMPLE 2

29.9 parts of o-phenylphenol are added at room temperature, with vigorous stirring, to 100 parts of an aqueous polymer solution of the following composition:

| | |
|---|---|
| 31.1% | by weight of a water-soluble copolymer containing 128.7 meqs of chemically bonded tertiary ammonium groups per 100 g of polymer |
| 10.6% | by weight of butyl glycol |
| 2.4% | by weight of acetic acid |
| 55.9% | by weight of distilled water |
| 100% | by weight. |

A stable emulsion of the following composition is obtained:

| | |
|---|---|
| 18.5% | by weight of a water-soluble copolymer |
| 6.3% | by weight of butyl glycol |
| 1.6% | by weight of acetic acid |
| 23.0% | by weight of o-phenylphenol |
| 50.6% | by weight of distilled water |
| 100% | by weight | pH value of the emulsion: 6.22
viscosity: 103 mPas.

The ratio between the equivalents of ammonium groups to moles of microbicide is 1:5.68.

The aqueous polymer solution used for the formulation of the o-phenylphenol had been obtained as follows:

a) 1,726 parts of glycidyl methacrylate, 316 parts of styrene, 40.3 parts of azo-bis-isobutyronitrile and 17.5 parts of dodecanethiol were copolymerised in 900.2 parts of butyl glycol, as described in Example 1a). A copolymer solution with a solids content of 68.8% by weight was obtained; the flow viscosity of the copolymer solution diluted to 40% by weight with dimethylformamide was 34 seconds; the epoxide equivalent was 172.8.

b) 2,725 parts of the copolymer solution obtained in a) were reacted with 1,508.5 parts of Prifac 7968 under the conditions described in Example 1b) (acid number of the reaction product: 0.1).

The viscosity of the solution of the reaction product diluted to 40% by weight with dimethylformamide was: 88 seconds. Solids content: 76.6% by weight.

c) A solution of 240.5 parts of dimethylethanolamine and 162.5 parts of glacial acetic acid in 181.2 parts of butyl glycol was added with stirring, at 80° to 120° C., to 2,200 g of the solution of the reaction product obtained in b). The resulting reaction product had a content of ammonium groups of 128.7 milliequivalents per 100 g of copolymer. The values of the solution of the reaction product were: solid content: 74.6% by weight; flow viscosity of the solution of the reaction product diluted to 40% by weight with dimethylformamide: 88 seconds.

The reaction product was diluted to a solids content of 31.1% by weight by adding distilled water in portions. A clear solution of the following composition was obtained:

| | |
|---|---|
| 31.1% | by weight of a water-soluble copolymer containing 128.7 meqs of chemically bonded quaternary ammonium groups per 100 g of polymer |
| 10.6% | by weight of butyl glycol |
| 2.4% | by weight of acetic acid |
| 55.9% | by weight of distilled water |
| 100% | by weight |

The pH value of the polymer solution: 7.31;
Viscosity: 10,500 mPas

EXAMPLE 3

A 50% strength solution of a p-chloro-m-cresol/o-phenylphenol (2:3) mixture in butyl glycol is added at room temperature, with vigorous stirring, to 100 parts of an aqueous polymer solution of the following composition:

| | |
|---|---|
| 32.7% | by weight of a water-soluble copolymer containing 189.8 meqs of chemically bonded tertiary ammonium groups per 100 g of polymer |
| 10.9% | by weight of methoxypropanol |
| 3.7% | by weight of acetic acid |

-continued

| 52.7% | by weight of distilled water |
|---|---|
| 100% | by weight. |

A stable solution of the following composition is obtained:

| 19.2% | by weight of a water-soluble copolymer containing 189.8 meqs of chemically bonded tertiary ammonium groups per 100 g of polymer |
|---|---|
| 6.3% | by weight of methoxypropanol |
| 9.2% | by weight of butyl glycol |
| 2.2% | by weight of acetic acid |
| 9.2% | by weight of the 2:3 mixture of p-chloro-m-cresol and o-phenylphenol |
| 53.9% | by weight of water |
| 100.0% | by weight | pH value of the emulsion: ~5,0; viscosity: ~350 mPas

The ratio of the equivalents of ammonium groups to moles of microbicide is 1:1.59.

The aqueous polymer solution used for the preparation of the emulsion had been obtained as follows:

a) 742.4 parts of styrene, 331.7 parts of methyl methacrylate, 35.1 parts of n-butyl acrylate, 935.7 parts of glycidyl methacrylate, 45.9 parts of azo-bis-isobutyronitrile and 20 parts of dodecanethiol were copolymerised in 904.4 parts of methoxypropanol under the conditions described in Example 1a). After a reaction time of 8 hours at 110° C. a copolymer solution having a solids contents of 70.6% by weight was obtained.

Epoxide equivalent of the polymer: 172.8; Viscosity of the copolymer solution diluted to 40% by weight with methoxypropanol: 86 seconds.

b) 2,766.2 parts of the copolymer solution obtained in a) were reacted with 282.1 parts of Prifac 7968 under the conditions described in Example 1b) (acid number of the reaction product: 1.0). Solids content of the reaction solution: 72.7% by weight; flow viscosity of the reaction product diluted to 40% by weight with methoxypropanol: 75 seconds.

c) 2,600 parts of the reaction solution obtained in b) were reacted with 345 parts of diethylamine under the conditions described in Example 1c). The amine excess of 31.4 parts was distilled off under reduced pressure.

The resulting polymer containing tertiary amino groups had a content of amino groups of 189.8 meqs per 100 g of polymer.

Solids content of the reaction solution: 75.0% by weight; viscosity of the reaction solution diluted to 40% by weight with methoxypropanol: 108 seconds.

After all the amino groups present in the polymer had been neutralised with acetic acid the solution of the reaction product was diluted to a solids content of 32.7% by weight by adding water in portions. The clear solution had a pH value of 6.1 and a viscosity of 24,700 mPas. Composition of the aqueous solution:

| 32.7% | by weight of a water-soluble copolymer containing 189.8 meqs of tertiary ammonium groups per 100 g of polymer |
|---|---|
| 10.9% | by weight of methoxypropanol |
| 3.7% | by weight of acetic acid |
| 52.7% | by weight of distilled water |
| 100% | by weight |

EXAMPLE 4

A 34.2% solution of 5,5'-dichloro-2,2'-dihydroxydiphenylmethane in butyl glycol was added at room temperature, with vigorous stirring, to 67.3 parts of the aqueous polymer solution obtained according to Example 3c). Then a further 7 parts of water were added. A stable emulsion of the following composition was obtained:

| 22.0% | by weight of water-soluble copolymer containing 189.8 meqs of chemically bonded tertiary ammonium groups per 100 g of polymer |
|---|---|
| 7.3% | by weight of methoxypropanol |
| 2.5% | by weight of acetic acid |
| 8.8% | by weight of 5,5'-dichloro-2,2'-dihydroxydiphenylmethane |
| 16.9% | by weight of butyl glycol |
| 42.5% | by weight of water |
| 100% | by weight | pH of the emulsion: ~5.0; viscosity: ~1300 mPas

The ratio of equivalents of ammonium groups to moles of microbicide is 1:0.79.

EXAMPLE 5

42.5 parts of o-phenylphenol are added slowly at room temperature, with vigorous stirring, to 100.0 parts of an aqueous polymer solution of the following composition:

| 32.5% | by weight of a water-soluble copolymer containing 298.3 meqs of tertiary ammonium groups per 100 g of polymer |
|---|---|
| 8.6% | by weight of methoxypropanol |
| 6.0% | by weight of acetic acid |
| 52.9% | by weight of distilled water |
| 100% | by weight. |

A stable emulsion of the following composition is obtained:

| 22.8% | by weight of a water-soluble copolymer containing 298.3 meqs of chemically bonded tertiary amino groups per 100 g of polymer |
|---|---|
| 6.9% | by weight of methoxypropanol |
| 4.2% | by weight of acetic acid |
| 37.1% | by weight of distilled water |
| 29.8% | by weight of o-phenylphenol |
| 99.9% | by weight | pH of the emulsion: 5.36; viscosity: 99 mPas

The ratio of equivalents of ammonium groups to moles of microbicide is 1:2.58.

The emulsion can be diluted with water without difficulty to active compound concentrations of 1 to 5% by weight.

The aqueous polymer solution used for the preparation of the emulsion had been obtained as follows:

A mixture of 672 parts of styrene, 300.2 parts of methyl methacrylate, 31.8 parts of n-butyl acrylate, 936.4 parts of N,N-dimethylaminoethyl methacrylate, 41.6 parts of Porophor-N and 18.1 parts of dodecanethiol was added dropwise at 110° C., in the course of 2.5 hours, to 500 parts of methoxypropanol. The polymerisation mixture was stirred at 110° C. for 6 hours.

The solids content of the polymerisation solution was then 79.1% by weight, the flow viscosity of the copolymer solution diluted to 40% by weight with methoxypropanol was 47 seconds. Content of tertiary amino groups in the copolymer: 298.3 milliequivalents per 100 g of copolymer.

After neutralisation of the amino groups with acetic acid the copolymer solution was diluted to a solids content of 32.5% by weight by the addition of water in portions. A clear solution of the following composition was obtained:

| | |
|---|---|
| 32.5% | by weight of water-soluble copolymer containing 298.3 meqs of chemically bonded tertiary ammonium groups per 100 g of polymer |
| 6.0% | by weight of acetic acid |
| 8.6% | by weight of methoxypropanol |
| 52.9% | by weight of distilled water |
| 100.0 | %by weight |

The pH value of the solution was 5.36 and the viscosity was 6,320 mPas.

EXAMPLE 6

Wood chips of pine splintwood were impregnated by immersion
a) in the formulation described in Example 1, diluted with water to an active compound content of 1.5% by weight of o-phenylphenol
b) in the formulation described in Example 1, diluted with water to an active compound content of 4.5% by weight of o-phenylphenol
c) in an aqueous solution containing 1.5% by weight of the potassium salt of o-phenylphenol and
d) in an aqueous solution containing 4.5% by weight of the potassium salt of o-phenylphenol.

After the chips had been dried, the decrease in the content of active compound by exposure to evaporation was determined.

This exposure to evaporation was performed in a wind tunnel in accordance with DIN EN 73 using a wind tunnel unit of type WK 320-313 from PVP GmbH. The wind speed was 1±0.1 m/second and the temperature of the air current was 40±2° C.

To determine the properties under exposure to evaporation, after being impregnated the wood chips were kept in a fume cupboard for 24 hours. The chips were then distributed amongst the four chambers of the wind tunnel, each chamber containing chips impregnated with one of the solutions.

After treatment in the wind tunnel for 5 weeks, analysis of the wood chips gave the following recovery rate for the o-phenylphenol:

TABLE 1
Recovery rate after 5 weeks in a wind tunnel
a) 72 to 80%
b) 82 to 83%
c) 10%
d) 10%

EXAMPLE 7

Samples of cotton fabric were impregnated by immersion
a) in the aqueous polymer solution obtained according to Example 1c
b) in the o-phenylphenol emulsion prepared according to Example 1
c) in an aqueous solution of the potassium salt of o-phenylphenol.

The concentrations of the impregnating solutions were chosen so that each sample of cotton fabric contained the same quantity of o-phenylphenol, that is to say 0.5% by weight, based on the fabric weight.

The impregnated fabric samples were dried at room temperature and then heat-treated at 120° C. for 10 minutes and at 150° C. for 5 minutes. Then the microbicidal activity of the samples of material against the test microorganism *Aspergillus niger* and *Chaetomium globosum* was determined by the agar diffusion test. The evaluation was performed after storage for 7 days at 30° C.

The values determined for the individual fabric samples are assembled in the following table:

The evaluation numbers in the table have the following meaning:

0 = inadequate action
   Test organisms have grown over >25% of the surface of the test specimens.
1 = moderate action
   Test organism have grown over <25% of the surface of the test specimens.
2 = good action
   The test specimens are free from growth, without any inhibiting areola or inhibiting zones being formed.
3 = very good action
   The test specimens are free from growth, and in addition an inhibiting areola or inhibiting zone has been formed.

TABLE 2
| Drying | Evaluation |
|---|---|
| a) Room temperature | 0 |
| 150° C. | 1 |
| b) Room temperature | 3 |
| 150° C. | 3 |
| c) Room temperature | 3 |
| 150° C. | 1 |

It is clear from Table 2 that the formulation according to Example 1 produces a very good microbicidal finish both at room temperature and at 150° C. In contrast, the alkaline formulation produces a microbicidal finish which loses activity very rapidly after exposure to heat, which can be seen from the marked decrease from 3 to 1. The water-soluble copolymer without any active compound displays moderate intrinsic activity after the intensified drying.

EXAMPLE 8

121.1 parts of molten o-phenylphenol are added dropwise at 50° C., with vigorous stirring, to 1000 parts of an aqueous polymer solution of the following composition:

| | |
|---|---|
| 57.3% | by weight of a water-soluble polyurethane containing 192.3 meqs of chemically bonded tertiary ammonium groups per 100 g of polycondensate |
| 7.5% | by weight of acetic acid |
| 35.2% | by weight of water |
| 100.0% | by weight. |

A clear solution of the following composition is obtained:

| | |
|---|---|
| 51.1% | by weight of a water-soluble polyurethane containing 192.3 meqs of chemically bonded tertiary ammonium groups per 100 g of polycondensate |
| 6.7% | by weight of acetic acid |
| 31.4% | by weight of water |

17

-continued

| 10.8% by weight of o-phenylphenol |
| 100.0% by weight | pH value of the solution: 4.94;
viscosity: 42,700 mPas.

The ratio of equivalents of tertiary ammonium groups to moles of microbicide is 1:0.57. The solution can be diluted without difficulty with water to active compound concentrations of 1% by weight.

The aqueous polymer solution used had been obtained as follows:

617 parts of isophorone diisocyanate were added dropwise at 60° C. in the course of 3 hours to a mixture of 177.9 parts of tetraethylene glycol, 255.1 parts of N-methyldiethanolamine and 500 parts of tetrahydrofuran contained in a stirring apparatus equipped with reflux condenser, a dropping funnel and a thermometer. After stirring the reaction mixture for 9 hours at 60° to 80° C. the content of isocyanate groups had fallen to <0.1%. After distilling off 290 parts of tetrahydrofuran (in a water jet vacuum) the amino groups present in the reaction mixture were neutralized by adding glacial acetic acid. The neutralization mixture was then adjusted to a polymer content of about 60% by weight by adding distilled water. Then the remaining tetrahydrofuran was expelled from the neutralization mixture by passing through nitrogen (30 l/N$_2$/h) for 16 hours at 60° C. The remaining polymer solution had a solids content of 57.3% by weight (determined by heating a sample for 1 hour at 120° C. and weighing out the non-volatile constituents). Content of tertiary ammonium groups in the polymer: 192.3 meqs per 100 g of polyurethane.

pH value of the polymer solution: 5:22;
viscosity: 13,300 mPas.

By adding water it was possible to dilute the polymer solution to a polymer content of as low as 10% by weight.

EXAMPLE 9

66 parts of molten o-phenylphenol are added dropwise at about 60° C., with vigorous stirring, to 500 parts of an aqueous polymer solution of the following composition:

| 35.0% by weight of a water-soluble polyurethane containing 171.1 meqs of chemically bonded tertiary ammonium groups per 100 g of polymer |
| 4.0% by weight of acetic acid |
| 45.7% by weight of water |
| 15.3% by weight of ethylene glycol monobutyl ether |
| 100.0% by weight. |

A clear, stable solution of the following composition is obtained:

| 31.5% by weight of water-soluble polyurethane containing 171.1 meqs of chemically bonded tertiary ammonium groups per 100 g of polymer |
| 3.6% by weight of acetic acid |
| 41.1% by weight of water |
| 13.7% by weight of ethylene glycol monobutyl ether |
| 10.1% by weight of o-phenylphenol |
| 100.0% by weight | pH value of the solution: 5.18;
viscosity: 2,440 mPas.

18

The ratio of equivalents of ammonium groups to moles of microbicide is 1:0.88. A stable emulsion is obtained from the solution on further dilution with water.

The aqueous polymer solution used had been obtained as follows:

1241.4 parts of ®Lekutherm X 20 (standard liquid resin based on the glycidyl ether of bisphenol A, epoxide equivalent weight: 185 to 200) were reacted at 140° C. in a stirring apparatus with 358.6 parts of soy-bean oil fatty acid to an acid number of 2.5 mg KOH/g.

399.1 parts of diethylamine were added at 50° to 120° C. in the course of 75 minutes to 1450 parts of the resulting reaction product containing epoxide groups. After the amine had been added the reaction mixture was stirred for 4 hours at 100° to 105° C. Content of amino groups in the reaction product: 251.7 meqs per 100 g of polymer.

453 parts of isophorone diisocyanate were added dropwise in the course of 4 hours to 1787.1 parts of this reaction product containing amino groups. The reaction mixture was heated at 150° C. for 3 hours (content of NCO groups: 0%; content of amino groups: 190.9 meqs per 100 g of polymer). Flow viscosity (according to DIN 53 211) of the polymer diluted with dimethylformamide to form a 60% strength solution: 37 seconds.

The amino groups of the polyurethane were then neutralised by adding glacial acetic acid and the neutralisation product was diluted to a polymer content of 41.3 by adding distilled water. The content of tertiary ammonium groups per 100 g of polyurethane is 171.2 meqs.

pH value of the solution: 5.35;
viscosity: 13,600 mPas.

The 41.3% strength by weight solution was diluted to a polymer content of 35.0% by weight by adding ethylene glycol monobutyl ether.

EXAMPLE 10

113.6 parts of molten o-phenylphenol are added dropwise at 50° C., with vigorous stirring, to 1000 parts of an aqueous polymer solution of the following composition:

| 52.5% by weight of a water-soluble polyurethane containing 255.4 meqs of chemically bonded quaternary ammonium groups per 100 g of polymer |
| 47.5% by weight of water |
| 100.0% by weight. |

A clear solution of the following composition is obtained:

| 47.1% by weight of a water-soluble polyurethane containing 255.4 meqs of chemically bonded quaternary ammonium groups per 100 g of polymer |
| 42.7% by weight of water |
| 10.2% by weight of o-phenylphenol |
| 100.0% by weight | pH value of the solution: 7.34;
viscosity: 887 mPas.

The ratio of equivalents of quaternary ammonium groups to moles of microbicide is 1:0.5. The solution can be diluted with water to form a stable emulsion.

The aqueous polymer solution used had been obtained as follows:

333 parts of isophorone diisocyanate were added dropwise with stirring at 70° C. in the course of 3 hours to 267 parts of N,N-dimethylethanolamine contained in a stirring apparatus equipped with a reflux condenser, contact thermometer and dropping funnel. The reaction mixture was stirred for 1.5 hours (content of free NCO groups: 0; content of amino groups: 494.3 meqs per 100 g of reaction product).

590 parts of the resulting reaction product containing amino groups were neutralised at 90° C. with 177 parts of glacial acetic acid. 387.6 parts of ®Epikote 812 were then added dropwise to the neutralisation mixture at 60° to 105° C. in the course of 3 hours. To ensure adequate stirrability 600 parts of tetrahydrofuran were added during the reaction.

The resulting solution of the polymer in tetrahydrofuran was then diluted with water to a polymer content of about 52% by weight. Then the tetrahydrofuran was expelled from the polymer solution by introducing an intensive stream of nitrogen (30 l N$_2$/h) at 60° C. over a period of 13 hours.

Polymer content of the resulting solution: 52.2% by weight;
Viscosity: 331 mPas;
pH value: 8.08;
Content of chemically bonded quaternary ammonium groups: 255.4 meqs per 100 g of polymer.

EXAMPLE 11

Samples of cotton fabric were impregnated by immersion
a) in the aqueous polymer solution obtained according to Examples 8 and 9
b) in the o-phenylphenol emulsion prepared according to Examples 8, 9 and 10
c) in an isopropanol solution of the o-phenylphenol.

The concentrations of the impregnating solutions were chosen so that equal quantities of o-phenylphenol were contained in the individual samples of cotton fabric, that is to say 0.25 and 0.5% by weight, based on the weight of the fabric samples.

The impregnated fabric samples were dried at room temperature and then heat-treated for 20 minutes at 150° C. Then the microbicidal activity of the fabric samples against the test microorganism *Aspergillus niger* was determined by an agar diffusion test. The evaluation was performed after 7 days of storage at 25° C.

The values determined for the individual fabric samples are assembled in the following table.

The evaluation figures have the same meaning as in Table 2.

TABLE 3

| Formulation employed | % active compound | drying RT/20' | 150° C. |
|---|---|---|---|
| o-phenylphenol in isopropanol | 0.25 | 1-2 | 0 |
|  | 0.50 | 2-3 | 1-2 |
| according to Example 8 | — | 0 | 1 |
|  | 0.25 | 3 | 2 |
|  | 0.51 | 3 | 3 |
| according to Example 9 | — | 0 | 0 |
|  | 0.25 | 2-3 | 2 |
|  | 0.50 | 3 | 2-3 |
| according to Example 10 | 0.25 | 3 | 3 |
|  | 0.50 | 3 | 3 |

EXAMPLE 12

Samples of cotton fabric were impregnated by immersion as described in Example 4. The impregnated fabric samples were dried at room temperature and then heat-treated for 20 minutes at 150° C. Then the samples of cotton fabric were washed for 20 to 60 minutes. The microbicidal activity of the samples of fabric against the test microorganism *Aspergillus niger* was then determined by an agar diffusion test. The evaluation was again carried out after a 7-day incubation period at 25° C. The results obtained are listed in the following table:

TABLE 4

| Formulation employed | % active compound | washing 20' | 60' |
|---|---|---|---|
| o-phenylphenol in isopropanol | 0.25 | 0/0 | 0/0 |
|  | 0.50 | 1/1 | 0/1 |
| according to Example 8 | — | 0/1 | 0-1/1 |
|  | 0.25 | 2/2 | 2/2 |
|  | 0.51 | 3/3 | 3/3 |
| according to Example 9 | — | 0/0 | 0/0 |
|  | 0.25 | 2/1 | 2/1 |
|  | 0.50 | 3/2 | 3/2 |
| according to Example 10 | 0.25 | 2/2 | 0/0 |
|  | 0.49 | 3/3 | 1/1-2 |

It is clear from Table 3 that the formulations according to Examples 8, 9 and 10 retain their good to very good action both at room temperature and after being heated for 20 minutes at 150° C. It is also particularly noteworthy that high degrees of activity are obtained with low contents of active compound, such as, for example, 0.25%. After being dried at room temperature, the isopropanol formulations only display good to very good microbicidal activity at contents of higher than 0.5%. Where the original active compound content is 0.25% no microbicidal activity can be detected after 20 minutes heat treatment. Where the original active compound content is 0.5% only moderate to good activity results.

Table 4 clearly shows the improved fixation obtained with the formulations according to Examples 8, 9 and 10. Whilst the fabric samples treated with the isopropanol formulation lose their microbicidal activity almost completely during washing, the samples treated with the formulations according to the invention display good to very good activities.

What is claimed is:

1. A water-containing an water-dilutable microbicidal formulation comprising water, an effective amount of a microbicide, and a water-dispersible polymer having a content of 70-500 meqs of chemically bonded tertiary, quaternary or tertiary and quaternary ammonium groups per 100 g of polymer, the polymer containing chemically bonded radicals of mono- or polyunsaturated fatty acids.

2. A formulation according to claim 1, wherein the water-dispersible polymer has a content of chemically bonded tertiary, quaternary or tertiary and quaternary ammonium groups of 100 to 400 meqs per 100 g of polymer.

3. A formulation according to claim 1, wherein the water-dispersible polymer is a poly(meth)acrylate.

4. A formulation according to claim 3, wherein the water-dispersible poly(meth)acrylate is a product obtained by reacting a copolymer of styrene, methyl methacrylate and glycidyl methacrylate or a copolymer of styrene, methyl methacrylate, glycidyl methacrylate and n-butylacrylate with 5–40% by weight of an unsaturated fatty acid and 5–25% by weight of diethylamine or dimethyl-(1-hydroxyethyl)-ammonium acetate, the percent by weight in each case being based on the total weight of the polymer.

5. A formulation according to claim 1, additionally containing an organic solvent.

6. A formulation according to claim 1, wherein the microbicide is a phenolic microbicide.

7. A method for protecting industrial materials from microbial attack which comprises contacting the industrial material with an effective amount of the formulation of claim 1.

8. A method for protecting industrial materials from microbial attack which comprises contacting the industrial material with an effective amount of the formulation of claim 5.

* * * * *